US00PP24463P2

(12) United States Plant Patent
Zlesak

(10) Patent No.: US PP24,463 P2
(45) Date of Patent: May 20, 2014

(54) LARGE-FLOWERED CLIMBER ROSE PLANT NAMED 'ZLEELTONSTRACK'

(50) Latin Name: *Rosa hybrida*
Varietal Denomination: ZLEEltonStrack

(76) Inventor: David Charles Zlesak, St. Paul, MN (US)

( * ) Notice: Subject to any disclaimer, the term of this patent is extended or adjusted under 35 U.S.C. 154(b) by 101 days.

(21) Appl. No.: 13/573,072

(22) Filed: Aug. 20, 2012

(51) Int. Cl.
*A01H 5/00* (2006.01)

(52) U.S. Cl.
USPC ..... Plt./111; Plt./101; Plt./109

(58) Field of Classification Search
USPC ..... Plt./111, 101, 109
See application file for complete search history.

*Primary Examiner* — Susan McCormick Ewoldt

(57) ABSTRACT

Large flowered climbing rose plant having a large plant habit that is upright and spreading; very vigorous growth; semi-double to double flowers typically borne in clusters of 5 or more; orange flower buds that open to apricot colored blooms; prolific bloom in mid to late spring and sporadic recurrent flowering in summer; resistance to major fungal diseases; extreme winter hardiness and ability to root and grow vigorously from softwood and semi-hardwood cuttings.

8 Drawing Sheets

Latin name of the plant claimed: *Rosa hybrida.*
Variety denomination: 'ZLEEltonStrack'.

BACKGROUND OF THE INVENTION

The primary objective of making the cross that led to 'ZLEEltonStrack' was to combine the traits of yellow flower color and repeat flowering during the growing season from the female parent and extreme winter hardiness and health from the male parent. The pollination occurred in late spring 2000. Seed from this cross germinated during the winter of 2000/2001 and 'ZLEEltonStrack' was identified as a superior seedling among the population and was first asexually propagated during the Summer of 2001.

The present invention relates to a new and distinct variety of rose plant of the large-flowered climber commercial class designated 'ZLEEltonStrack'. 'ZLEEltonStrack' was originated by me by crossing the miniature rose 'CURlem' as the female parent and an unnamed seedling selection, 1999-2, as the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Large plant habit that is upright and spreading;
2. Very vigorous growth;
3. Semi-double to double flowers typically borne in clusters of 5 or more;
4. Orange flower buds that open to apricot colored blooms;
5. Prolific bloom in mid to late spring and sporadic recurrent flowering in summer;
6. Resistance to major fungal diseases;
7. Extreme winter hardiness;
8. Ability to root and grow vigorously from softwood and semi-hardwood cuttings.

Asexual reproduction of this new variety by rooting softwood and semi-hardwood cuttings, as performed at St. Paul, Minn., shows that the foregoing and all other characteristics and distinctions come true to form and are established and transmitted through succeeding vegetative propagations.

COMPARISON WITH PARENTS

'ZLEEltonStrack' is larger than both its parents in flower and plant size and has apricot-colored petals. 'ZLEEltonStrack' can be trained as a traditional climbing rose against support structures or serve as a large free standing shrub. It has shown extreme cane hardiness without insulation in United States Department of Agriculture cold hardiness zone 3. 'ZLEEltonStrack' differs from its female parent, 'CURlem', in that 'CURlem' has double yellow blooms (over 25 petals) and is less cold hardy (plants of 'CURlem' have died overwinter due to cold in United States Department of Agriculture cold hardiness zone 4). 'ZLEEltonStrack' differs from its male parent, 1999-2, in that 1999-2 has single blooms (5 petals) that are light pink in color and is smaller in flower and plant size. Both 1999-2 and 'ZLEEltonStrack' have consistently survived with live canes without insulation in United States Department of Agriculture cold hardiness zone 3 and both have the potential for sporadic recurrent bloom under favorable growing conditions after the major flowering event in mid to late spring.

COMPARISON WITH SIMILAR VARIETY

The rose variety with the greatest similarity to 'ZLEEltonStrack' is 'William Baffin', a rose registered with the American Rose Society under the Hybrid Kordesii commercial class and commonly sold in commerce as a climbing rose. Both 'ZLEEltonStrack' and 'William Baffin' have similar growth habits and routine cane survival without insulation in United States Department of Agriculture cold hardiness zone 3. Both have one major display of flowers over a few week period in mid to late spring and then under favorable conditions have sporadic recurrent bloom. 'ZLEEltonStrack' differs from 'William Baffin' in that 'ZLEEltonStrack' has apricot colored flowers and 'William Baffin' has pink flowers. The flowers of 'ZLEEltonStrack' are larger than 'William Baffin' and typically have slightly fewer petals.

BRIEF DESCRIPTION OF THE DRAWINGS

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

Figure 1:
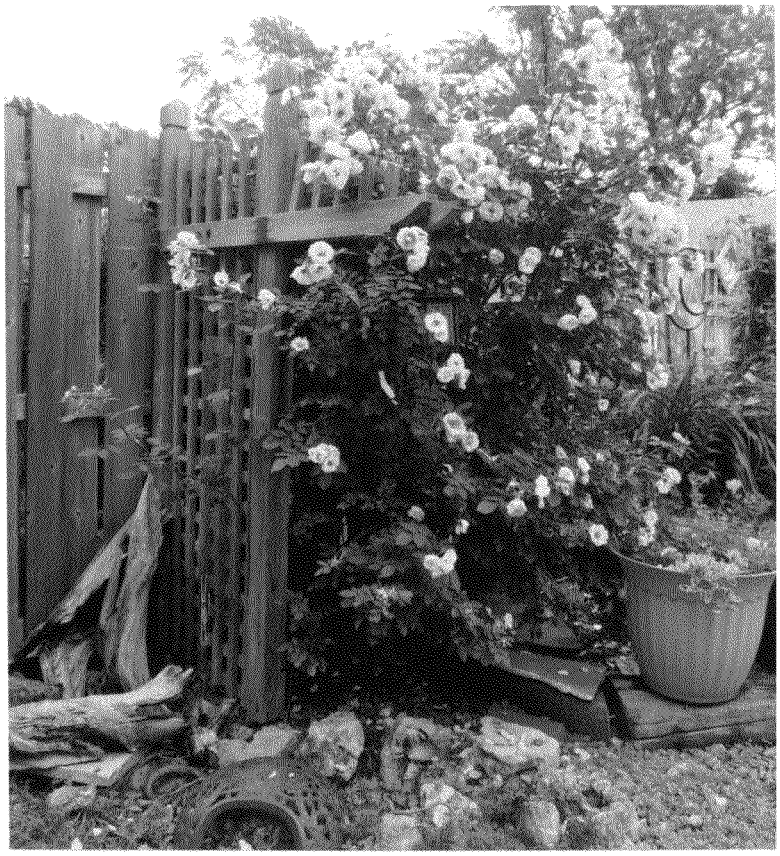
FIG. 1 illustrates a mature plant during its first cycle of bloom in June that has been routinely pruned and trained against a support structure.
Figure 2:
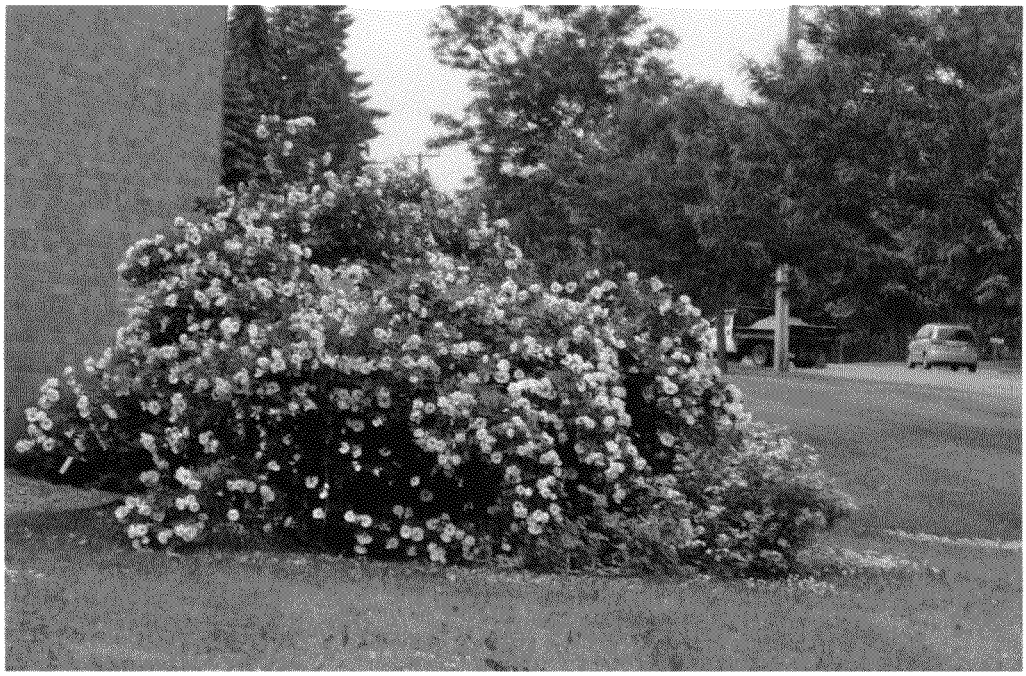
FIG. 2 illustrates a mature plant during its first cycle of bloom in June that has not been pruned and was allowed to grow as a free standing shrub.
Figure 3:
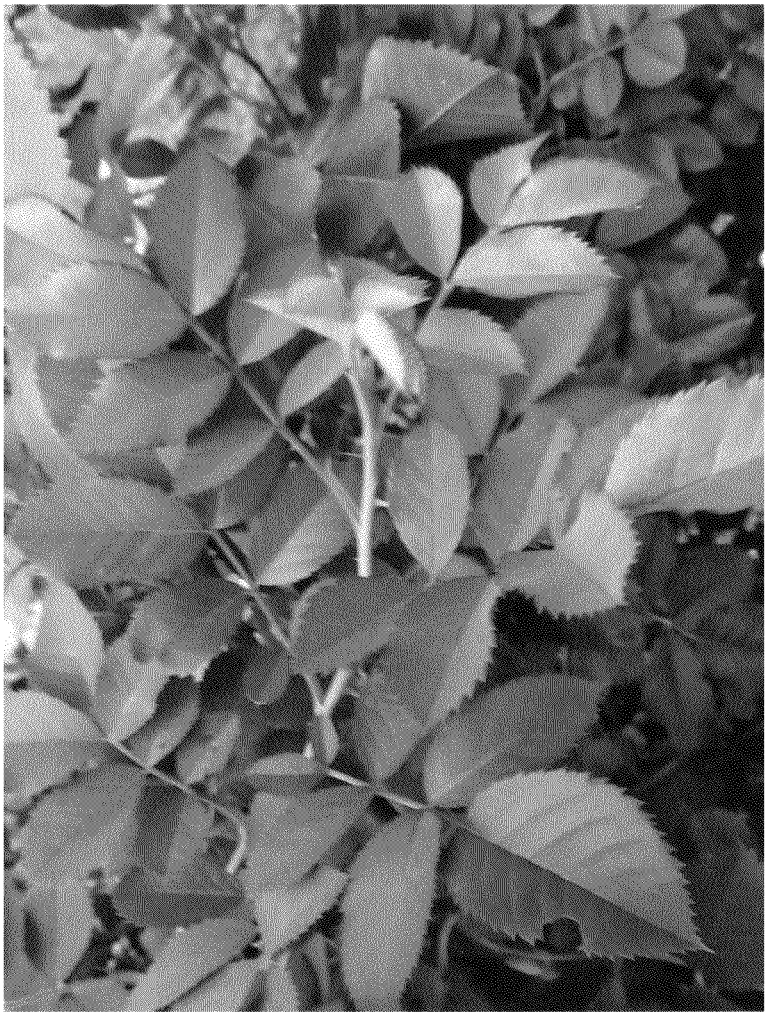
FIG. 3 illustrates new vegetative growth.
Figure 4:
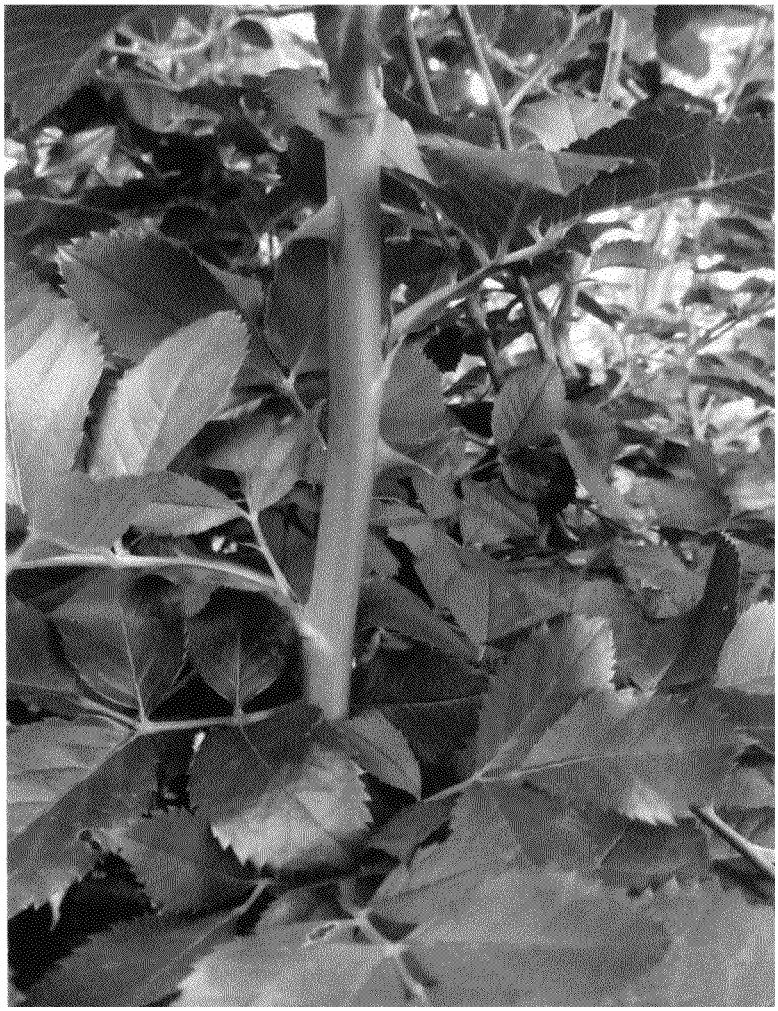
FIG. 4 illustrates a maturing stem with prickles.
Figure 5:
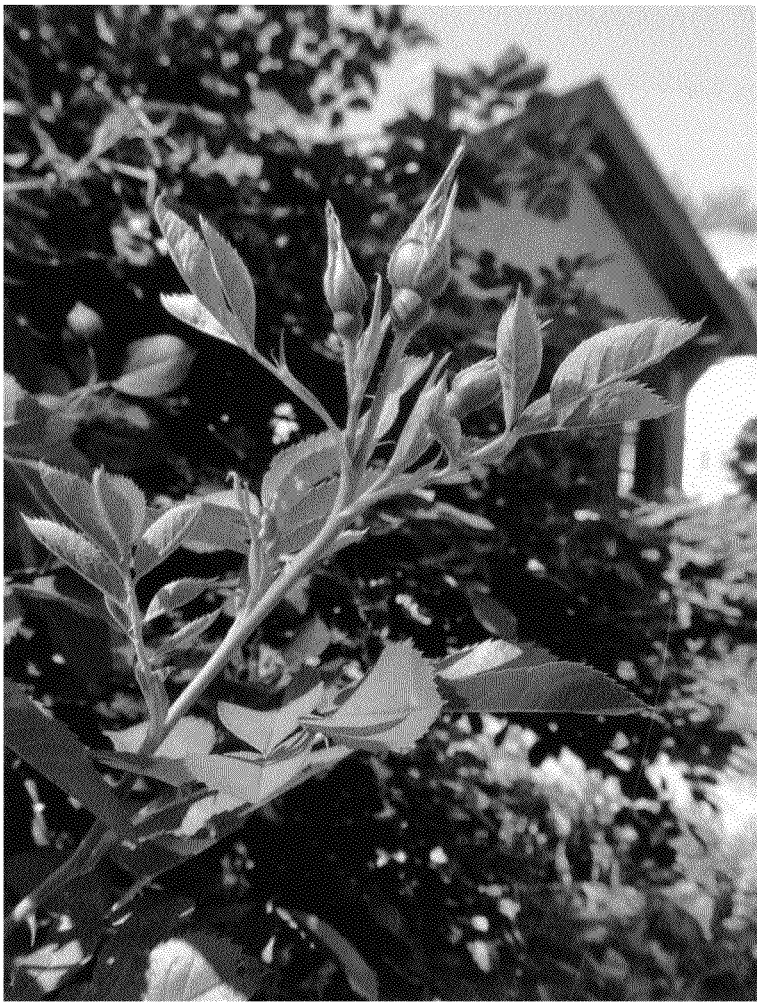
FIG. 5 illustrates developing flower buds.
Figure 6:
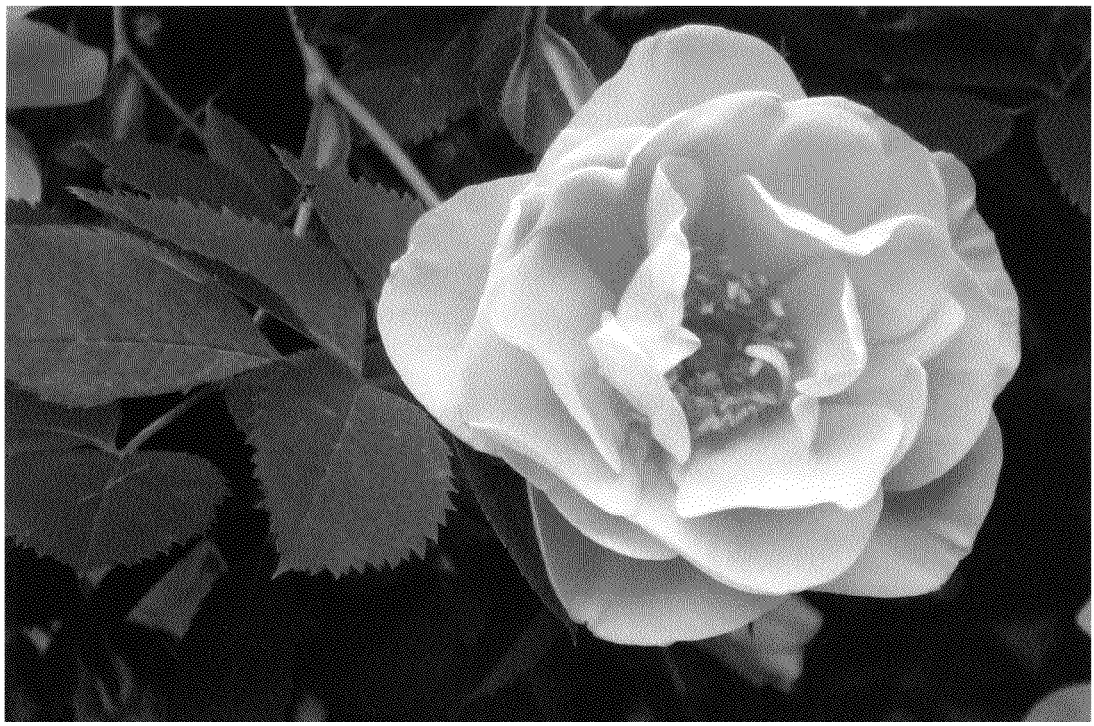
FIG. 6 illustrates a closeup of an open flower.
Figure 7:
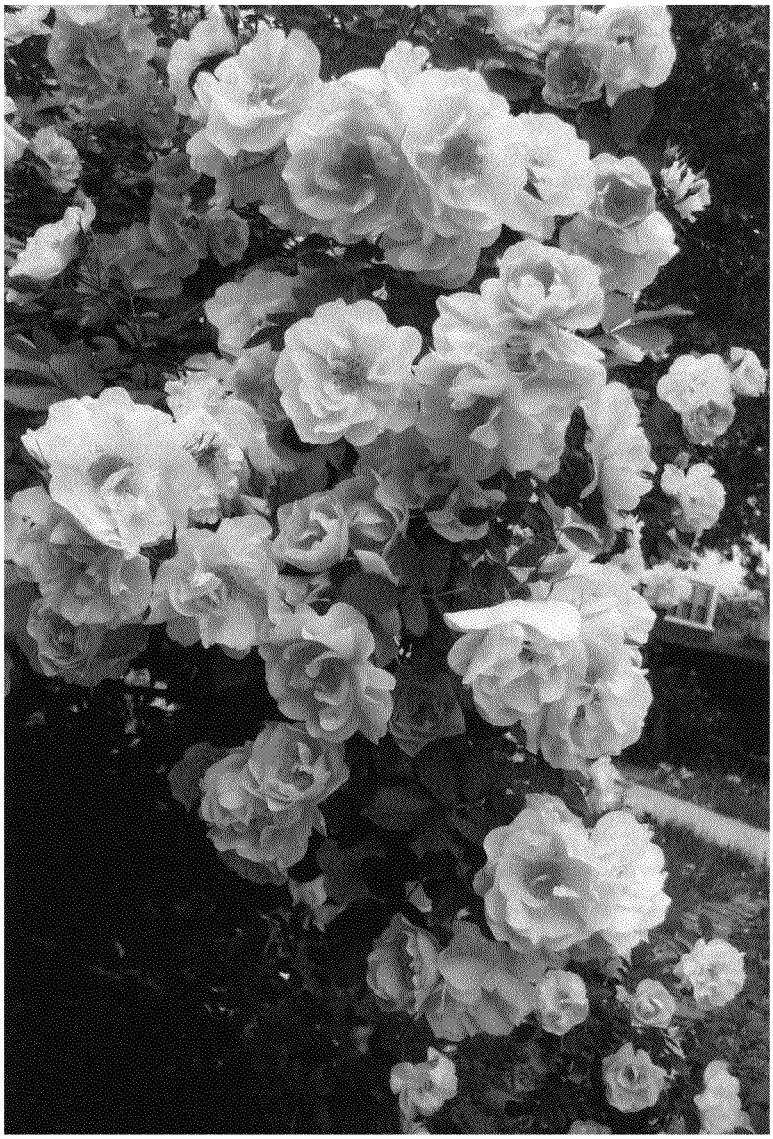
FIG. 7 illustrates multiple flowers at different stages of development.
Figure 8:
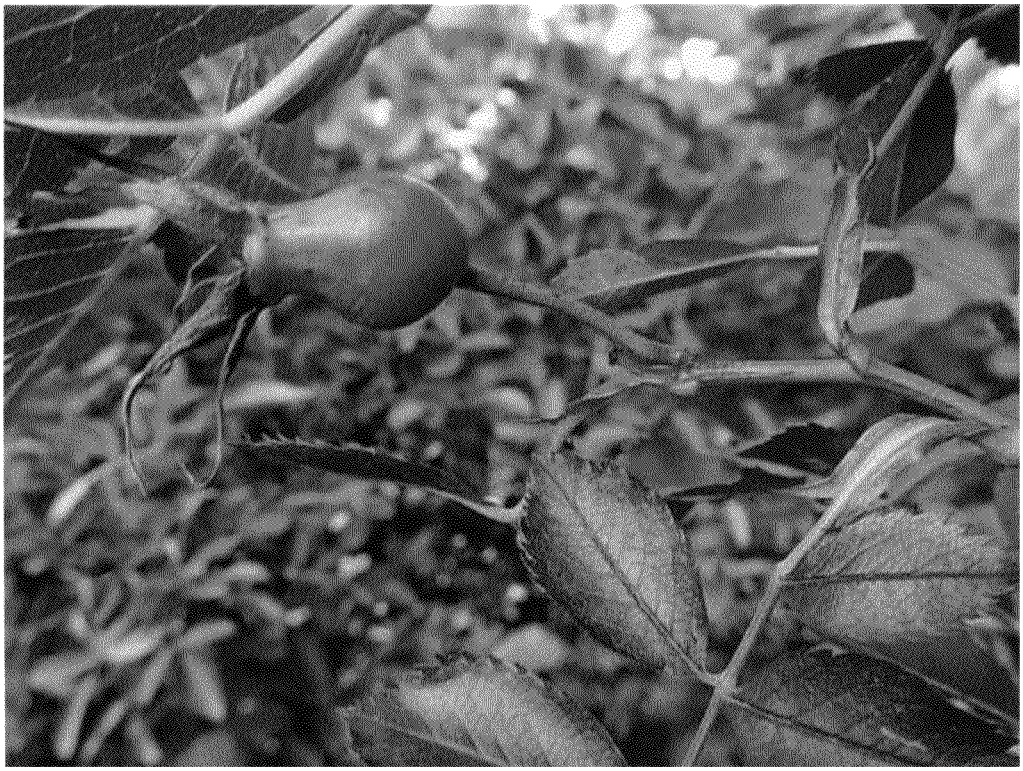
FIG. 8 illustrates a ripening hip.
Figure 9:
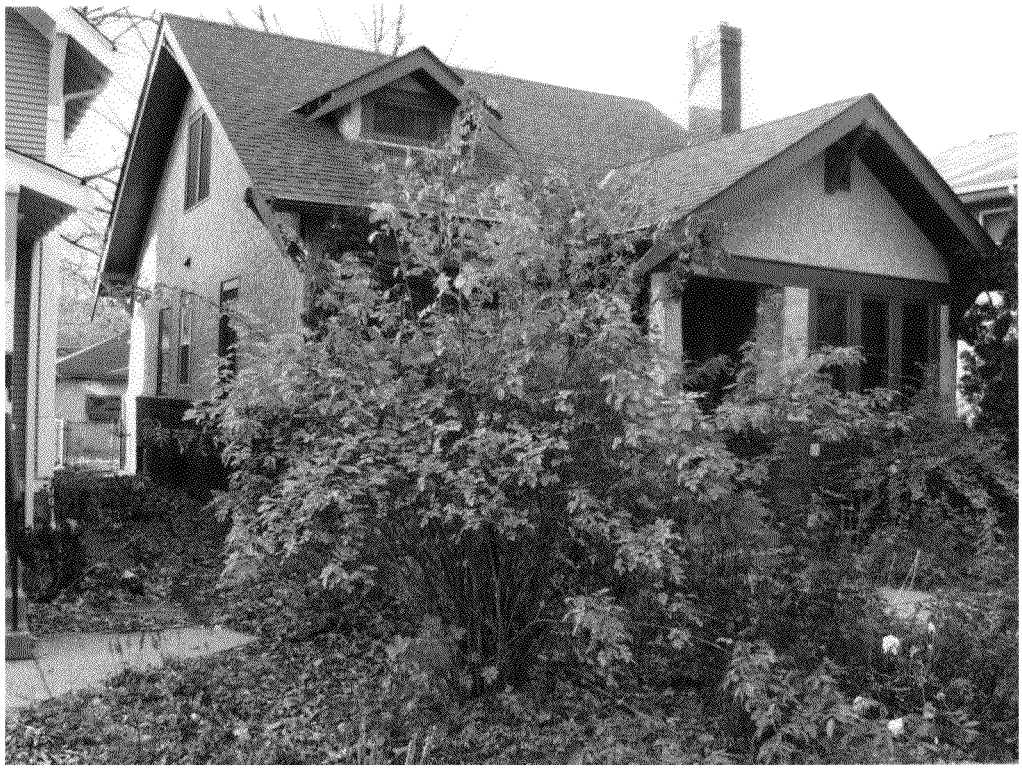
FIG. 9 illustrates golden fall foliage color on a mature plant.

The following is a detailed description of my new rose cultivar with color descriptions using terminology in accordance with The Royal Horticultural Society (London) Colour Chart (2001), except where ordinary dictionary significance of color is indicated. The phenotype of the new cultivar may vary with variations in environmental, climatic, and cultural conditions, as it has not been tested under all possible environmental conditions. Descriptions are based on observations of plants approximately seven years of age that were propagated from semi-hardwood cuttings and are not grafted onto rootstock.

Parentage:

*Seed parent.*—'CURlem'.

*Pollen parent.*—1999-2 An unnamed seedling never released for sale that is a cross of (*Rosa virginiana* Mill. open pollinated)×*Rosa laxa* Retzius.

Classification:

*Botanical.*—*Rosa hybrida.*

*Commercial.*—Large-flowered climber.

Flower:

*Blooming habit.*—Plants bloom abundantly over a few week period in late spring to early summer and then under favorable growing conditions has sporadic recurrent bloom.

Bud:

*Size.*—22-25 mm long and 14-16 mm in diameter when the petals start to unfurl.

*Form.*—The bud form is ovoid and pointed.

*Color.*—When sepals first divide, visible petal color is Orange-Red Group 31D. When half blown, the upper or adaxial sides of the petals are Yellow-Orange Group 19C. The lower or abaxial sides of the petals are Yellow-Orange Group 18D.

*Sepals.*—Color: Yellow-Green Group 144B on the abaxial side and Green Group 138C on the adaxial side. Length: 22-28 mm. Width: 6-8 mm. Shape: ovate to lanceolate with slightly acuminate tips. Surface texture: Adaxial, Hoary. Abaxial, Generally smooth with some very small glandular hairs that are about 1 mm long and 0.1 mm wide. There are three lightly appendaged sepals. There are two unappendaged sepals which have hoary edges.

*Receptacle.*—Color: Yellow-Green Group 143C. Shape: round. Size: Medium, about 8-10 mm wide and 8-10 mm long. Surface: generally glabrous with sporadic glandular hairs that are comparable to those on the adaxial side of the sepals.

*Peduncle.*—Length: Medium, averaging about 28-32 mm. Width: Medium, averaging 2 mm. Surface: Generally glabrous with some small glandulous hairs about 1-1.5 mm in length and 0.1 in width. Color: Yellow-Green Group 144B. Strength: Stiff, primarily erect.

Bloom:

*Size.*—Medium for commercial class. Typical open diameter is 80-85 mm.

*Borne.*—Typically clusters of 5-15 blooms are borne at the end of stems in small panicles.

*Stems.*—Strength: Medium to strong. Length of flowering stems: Typically about 20-25 cm in spring developing from vernalized axillary buds. Flowering stem diameter: Varies and is typically 4-6 mm. Larger stems arising from the base of the plant typically terminate in flowers in summer and are about 0.8-1.5 cm in diameter, while smaller stems arising from axillary buds of current season flowering stems within the plant canopy are typically 3-6 mm in diameter.

*Form.*—When blooms first open: Slightly cupped to flat. Petals often have slightly undulating margins.

*Permanence.*—Blooms retain their form to the end.

*Petalage.*—Typically a total of 14-22 petals and petaloids.

*Color.*—The adaxial sides of the petals are primarily Yellow-Orange Group 19C. The color of the abaxial side of the petals is primarily Yellow-Orange Group 18D.

*Discoloration.*—The general tonality of the bloom remains the same throughout the first day. At the end of the third day the adaxial and abaxial sides of the petals fade to Yellow-Orange Group 19D. Petals typically fall at day six.

*Fragrance.*—Slight. Character of fragrance: Spicy and very similar to its grandparent *Rosa laxa.*

Petals:

*Texture.*—Thick and satiny to the touch.

*Length.*—3.5-4.5 cm.

*Width.*—3.2-3.6 cm.

*Shape.*—Rounded to slightly obcordate.

*Margin.*—Entire to slightly undulating.

*Apex shape.*—Rounded to slightly obcordate and sometimes petals possess a small point in the axis.

*Base shape.*—Rounded to acute.

*Form.*—Flat or slightly cupped and sometimes margins are undulating.

*Arrangement.*—Multiple rows of overlapping petals.

*Petaloids.*—Roses have five true petals (except for *Rosa sericea* which typically has four) and all additional petal-like appendages are botanically petaloids. Petaloids are stamens or in some cases also pistils that develop into petal-like structures. However, petaloids that do not have obvious remnant stamen development are often called petals in common vernacular in United States Plant Patents and the popular press. 'ZLEEltonStrack', like typical roses, has five true petals, typically between 9 and 14 petaloids that look like a true petal, and often 3-5 petaloids that have some visible stamen development typically seen as an anther along one of the edges of a relatively narrow petal-like structure. The petaloids with anthers attached are found at the transition area in the bloom between the most petal-like petaloids and the stamens. Pistils in 'ZLEEltonStrack' do not develop into petaloids. The color of the petal-like portion of petaloids is typical for the color of a true petal.

*Persistence*.—Petals drop off cleanly before drying.

*Lastingness*.—On the plant: Medium (about 6 days). As a cut flower: Moderate (about 6 days).

Reproductive parts:

*Stamens*.—Number per flower: 120-160. Anthers — Size: Length before dehiscence: 2.5-3.0 mm, Width before dehiscence: 2.0 mm. Length after dehiscence: 2.0 mm. Width after dehiscence: 0.5 mm. Color: Before dehiscence: Yellow-Orange Group 14A. After dehiscence: Yellow-Orange Group 22A. Arrangement: Regular around styles. Filaments — Size: Length: 3-10 mm. Width: 0.25 mm. Color: Yellow-Orange Group 15A. Pollen — Color: Yellow-Orange Group 13A.

*Pistils*.—Number per flower: 35-50. Styles — Color: Green-Yellow Group 1C with highlights of Red Group 51D. Length: 3-6 mm. Stigmas — Color: Yellow Group 5B. Ovary — Color of immature ovary: Yellow-Green Group 145D.

*Hips*.—The fleshy portion of rose hips is hypanthium tissue and inside that tissue are achenes — individual, indehiscent fruits that have a single seed with a hard pericarp surrounding the embryo. Hips are typically minimally produced on 'ZLEEltonStrack' with less than 20% of blooms developing into hips. Sepals are persistent upon ripening. Hypanthium: Color immature: Green Group 146C. Color mature: Greyed-Orange N163A. Shape: Rounded to urceolate. Size: 15-20 mm long and 10-15 mm wide.

*Achenes (ripe)*.—Color: Greyed-Orange Group 164C. Shape: Ovate to oval. Size: 5-6 mm long and 4-5mm wide. Typically there are 1-5 achenes per hip.

Plant:

*Form*.—Vase shaped, large shrub. It can also be trained against a supportive structure such as a pillar, trellis, fence, or arbor and pruned to fit the desired space.

*Growth*.—Very vigorous and dense.

*Age at maturity*.—5 years.

*Mature plant*.—The typical mature height of an unsupported plant is about 3-4 m and width is slightly wider at 4-5 m.

Leaf:

*Form*.—Leaves are pinnately compound and have seven leaflets on a typical leaf.

*Arrangement*.—Leaves are alternately arranged on stems.

*Size*.—Medium to large (10-14 cm long and 8-11 cm wide).

*Quantity*.—Normal.

*Leaflet color*.—New foliage: Adaxial side: Yellow-Green Group 144A Abaxial side: Yellow-Green Group 146D. Old foliage: Adaxial side: Green Group 137B. Abaxial side: Yellow-Green Group 146B. In autumn under favorable conditions, leaves turn an attractive golden color (Yellow-Orange Group 21C) before abscission.

*Leaflet venation pattern*.—Pinnate reticulate.

*Leaflet venation color*.—The color of the veins is the same or very close to that of the overall leaf blade. New foliage: Adaxial side: Yellow-Green Group 144A Abaxial side: Yellow Green-Group 146D. Old foliage: Adaxial side: Green Group 137B. Abaxial side: Yellow-Green Group 146B.

*Leaflet size*.—Terminal leaflets: Medium (4.5-5.0 cm long and 3.0-3.5 cm wide). Non-terminal leaflets: Medium (4.0-4.5 cm long and 2.5-3.0 cm wide).

*Leaflet shape*.—Elliptic to slightly rounded.

*Leaflet base shape*.—Widely acute to rounded.

*Leaflet apex shape*.—Typically rounded to slightly acute.

*Leaflet texture*.—Semi-glossy and slightly rugose. On the adaxial side of leaflets the veins are slightly recessed and on the abaxial side they are slightly elevated relative to the general leaf blade.

*Leaflet edge*.—Serrated with typically medium-sized single serrations.

*Petiole*.—color. — The adaxial side is Yellow-Green Group 144A and the abaxial side is Yellow-Green Group 146D.

*Petiole rachis*.—Color: Same as petiole.

*Petiole underside*.—Generally smooth with periodic small prickles that are about 1.0-1.5 mm long and 0.1 to 0.2 mm wide and Yellow-Green Group 144A in color.

*Stipules*.—Medium (one is on each side of the petiole and are about 1.8-2.0 cm in length and 0.2-0.3 cm in width). Color: Adaxial side is Yellow-Green Group 137C and the abaxial side is Yellow-Green Group 146B. Edges: Several very small serrations (0.1-0.3 mm long).

*Disease resistance*.—Resistant to powdery mildew, black spot, and rust under normal growing conditions.

*Pest persistence*.—Not observed.

Stems:

*New stems*.—Color: Generally Yellow-Green Group 144B. Bark: Smooth.

*Old wood*.—Color: Yellow-Green Group 146C. Bark: Smooth.

Typical stem prickles:

*Quantity*.—Moderate.

*Form*.—Straight to slightly hooked downward.

*Length*.—7-9 mm.

*Width*.—0.3 cm near stem and narrowing to the tip.

*Color when young*.—Yellow-Green Group 144C.

*Color when mature*.—Grey-Brown Group 199D.

Small, secondary stem prickles:

*Quantity*.—Typically none.

Cytology:

*Ploidy*.—Teteraploid (2n=4x=28). Meristematic root tip cells in the stage of metaphase of mitosis were observed to have 28 chromosomes under a light microscope at 400× magnification.

Winter hardiness: Acclimated plants of 'ZLEEltonStrack' have displayed strong stem survival (complete to minor tip dieback) in United States Department of Agriculture cold hardiness zone 3 and warmer without insulation. In addition, 'ZLEEltonStrack' has consistently displayed very strong freeze tolerance on new growth in mid to late spring relative to other roses around it. In April 2007 a late freeze killed new stems and foliage on most roses in the inventor's St. Paul, Minn. garden, but stems and foliage of 'ZLEElton Strack' were not killed.

I claim:

1. A new and distinct variety of rose plant of the shrub class, substantially as herein shown and described, characterized particularly by its large plant habit that is upright and spreading; very vigorous growth; semi-double to double flowers typically borne in clusters of 5 or more; orange flower buds that open to apricot colored blooms; prolific bloom in mid to late spring and sporadic recurrent flowering in summer; resistance to major fungal diseases; extreme winter hardiness and ability to root and grow vigorously from softwood and semi-hardwood cuttings.

* * * * *